United States Patent
Katsevich

(10) Patent No.: US 7,197,105 B2
(45) Date of Patent: Mar. 27, 2007

(54) EFFICIENT IMAGE RECONSTRUCTION ALGORITHM FOR THE CIRCLE AND LINE CONE BEAM COMPUTED TOMOGRAPHY

(75) Inventor: Alexander Katsevich, Oviedo, FL (US)

(73) Assignee: Research Foundation of the University of Central Florida, Inc., Orlando, FL (US)

( * ) Notice: Subject to any disclaimer, the term of this patent is extended or adjusted under 35 U.S.C. 154(b) by 0 days.

(21) Appl. No.: 10/523,867

(22) PCT Filed: Apr. 23, 2004

(86) PCT No.: PCT/US2004/012536

§ 371 (c)(1), (2), (4) Date: Feb. 7, 2005

(87) PCT Pub. No.: WO2005/107598

PCT Pub. Date: Nov. 17, 2005

(65) Prior Publication Data

US 2006/0034417 A1    Feb. 16, 2006

Related U.S. Application Data

(63) Continuation-in-part of application No. 10/728,136, filed on Dec. 4, 2003, now Pat. No. 7,010,079, and a continuation-in-part of application No. 10/389,534, filed on Mar. 14, 2003, now Pat. No. 6,804,321, which is a continuation-in-part of application No. 10/389,090, filed on Mar. 14, 2003, now Pat. No. 6,771,733, which is a continuation-in-part of application No. 10/143,160, filed on May 10, 2002, now Pat. No. 6,574,299.

(60) Provisional application No. 60/430,802, filed on Dec. 4, 2002, provisional application No. 60/312,827, filed on Aug. 16, 2001.

(51) Int. Cl.
*A61B 6/03* (2006.01)

(52) U.S. Cl. ............................... 378/4; 378/901
(58) Field of Classification Search ............... 378/4–20, 378/901, 210

See application file for complete search history.

(56) References Cited

U.S. PATENT DOCUMENTS 4,426,578 A * 1/1984 Bradcovich et al. ... 250/363.08

(Continued)

OTHER PUBLICATIONS

Zeng et al., Implementation of Tuy's cone-beam inversion formula, 1994, Phys. Med. Biol., vol. 39, p. 493-507.*

(Continued)

*Primary Examiner*—Edward J. Glick
*Assistant Examiner*—John M. Corbett
(74) *Attorney, Agent, or Firm*—Brian S. Steinberger; Phyllis K. Wood; Law Offices of Brian S. Steinberger, P.A.

(57) ABSTRACT

Methods, systems and processes for providing efficient, accurate and exact image reconstruction using portable and easy to use C-arm scanning devices and rotating gantries, and the like. The invention can provide exact convolution-based filtered back projection (FBP) image reconstruction by combining a curved scan of the object and a line scan of the object. The curved scan can be done before or after the line scan. The curved scan can be less than or greater than a full circle about an object being scanned.

32 Claims, 8 Drawing Sheets

U.S. PATENT DOCUMENTS

| | | | |
|---|---|---|---|
| 5,170,439 A * | 12/1992 | Zeng et al. | 382/131 |
| 5,588,036 A * | 12/1996 | Fujise et al. | 378/146 |
| 5,834,780 A * | 11/1998 | Morgan et al. | 250/363.04 |
| 6,292,525 B1 | 9/2001 | Tam | 378/4 |
| 2005/0152494 A1* | 7/2005 | Katsevich | 378/62 |

OTHER PUBLICATIONS

Zeng et al., Interative Reconstruction with Attenuation Compensation from Cone-beam Projections Acquired via Nonplanar Orbits, Feb. 1997, IEEE Transactions on Nuclear Science, vol. 44, No. 1, p. 98-106.*

* cited by examiner

Fig. 9

Step 20. Finding families of lines for filtering.

It is assumed the x-ray source is located on the line $L$.

Step 21. Choose a discrete set of values of the parameter $s_t$ inside the interval $[s_t^{min}, s_t^{max}]$.

Step 22. For each $s_t$ chosen in Step 21 find a line tangent to the projected circle $\hat{C}$.

Step 23. The collection of lines constructed in Step 22 is the required set of lines.

Step 30

Fig. 10

Step 40. Preparation for filtering

Step 41. If the x-ray source is located on the line $L$, fix a filtering line $L_{fil} \in _{-1}$. If the x-ray source is on the circle $C$, fix $L_{fil} \in _{-2}$.

Step 42. Parameterize points on the said line by polar angle $\gamma$ in the plane through $y(s_0)$ and $L_{fil}$.

Step 43. Choose a discrete set of equidistant values $\gamma_j$ that will be used later for discrete filtering in Step 50.

Step 44. For each $\gamma_j$ find the unit vector $\beta_j$ which points from $y(s_0)$ towards the point on $L_{fil}$ that corresponds to $\gamma_j$.

Step 45. Using the CB projection data $D_f(y(q),\Theta)$ for a few values of $q$ close to $s_0$ find numerically the derivative $(\partial/\partial q)D_f(y(q),\Theta)|_{q=s_0}$ for all $\Theta = \beta_j$.

Step 46. Store the computed values of the derivative in computer memory.

Step 47. Repeat Steps 41-46 for all lines $L_{fil}$ identified in Step 20. This way we will create the processed CB data $\Psi(s_0,\beta_j)$

Step 50

Fig. 11

Step 50. Filtering

Step 51. Fix a filtering line $L_{flt}$. If the x-ray source is located on the line $L$, take $L_{flt} \in \_1$. If the x-ray source is located on the circle $C$, take $L_{flt} \in \_2$.

↓

Step 52. Compute FFT of the values of the said processed CB data computed in Step 40 along the said line.

↓

Step 53. Compute FFT of the filter $1/\sin\gamma$

↓

Step 54. Multiply FFT of the filter $1/\sin\gamma$ (the result of Step 53) and FFT of the values of the said processed CB data (the result of Step 52).

↓

Step 55. Take the inverse FFT of the result of Step 54.

↓

Step 56. Store the result of Step 55 in computer memory.

↓

Step 57. Repeat Steps 51-56 for all lines in the said family of lines. This will give the filtered CB data $\Phi(s_0, \beta_j)$.

↓

Step 60

Fig. 12

Step 60. Back-projection

Step 61. Fix a reconstruction point $x$, which represents a point inside the patient where it is required to reconstruct the image.

↓

Step 62. If $s_0 \in I_1(x) \cup I_2(x)$, then the said filtered CB data affects the image at $x$ and one performs Steps 63-68. If $s_0 \notin I_1(x) \cup I_2(x)$, then the said filtered CB data is not used for image reconstruction at $x$. In this case go back to Step 61 and choose another reconstruction point.

↓

Step 63. Find the projection $\hat{x}$ of $x$ onto the detector plane $DP(s_0)$ and the unit vector $\beta(s_0,x)$, which points from $y(s_0)$ towards $x$.

↓

Step 64. Identify filtering lines $L_{flt} \in \_1$ or $L_{flt} \in \_2$ (depending on where the x-ray source is located) and points on the said lines that are close to $\hat{x}$. This will give values of $\Phi(s_0,\beta_j)$ for $\beta_j$ close to $\beta(s_0,x)$.

↓

Step 65. With interpolation estimate the value of $\Phi(s_0,\beta(s_0,x))$ from the said values of $\Phi(s_0,\beta_j)$ for $\beta_j$ close to $\beta(s_0,x)$.

↓

Step 66. Compute the contribution from the said filtered CB data to the image being reconstructed at the point $x$ by multiplying $\Phi(s_0,\beta(s_0,x))$ by $-\delta_k(s_0,x)/(2\pi^2 |x-y(s_0)|)$ (see (8) for definition of $\delta_k(s_0,x)$).

↓

Step 67. Add the said contribution to the image being reconstructed at the point $x$ according to a pre-selected scheme for approximate evaluation of the integral in equation (10).

↓

Step 68. Go to Step 61 and choose a different reconstruction point $x$.

EFFICIENT IMAGE RECONSTRUCTION ALGORITHM FOR THE CIRCLE AND LINE CONE BEAM COMPUTED TOMOGRAPHY

This invention is a Continuation-In-Part of U.S. patent application Ser. No. 10/728, 136, filed Dec. 4, 2003, now U.S. Pat. No. 7,010,079 which claims the benefit of priority to U.S. Provisional Application Ser. No. 60/430,802 filed, Dec. 4, 2002, and is a Continuation-In-Part of U.S. patent application Ser. No. 10/389,534 filed Mar. 14, 2003, now U.S. Pat. No. 6,804,321 which is a Continuation-In-Part of Ser. No. 10/389,090 filed Mar. 14, 2003, now U.S. Pat. No. 6,771,733 which is a Continuation-In-Part of Ser. No. 10/143,160 filed May 10, 2002 now U.S. Pat. No. 6,574,299, which claims the benefit of priority to U.S. Provisional Application 60/312,827 filed Aug. 16, 2001.

FIELD OF INVENTION

This invention relates to computer tomography, and in particular to processes, methods and systems for reconstructing three dimensional images from the data obtained by a circle and line scan of an object, such as when the object first moves through a C-arm, and then the C-arm rotates around either a non moving or a moving object.

BACKGROUND AND PRIOR ART

Over the last thirty years, computer tomography (CT) has gone from image reconstruction based on scanning in a slice-by-slice process to spiral scanning to also include non-spiral scanning techniques such as those performed with C-arm devices, with all techniques and devices experiencing problems with image reconstruction.

From the 1970s to 1980s the slice-by-slice scanning was used. In this mode the incremental motions of the patient on the table through the gantry and the gantry rotations were performed one after another. Since the patient was stationary during the gantry rotations, the trajectory of the x-ray source around the patient was circular. Pre-selected slices through the patient were reconstructed using the data obtained by such circular scans.

From the mid 1980s to present day, spiral type scanning has become the preferred process for data collection in CT. Under spiral scanning a table with the patient continuously moves at a constant speed through the gantry that is continuously rotating about the table. At first, spiral scanning has used one-dimensional detectors, which receive data in one dimension (a single row of detectors). Later, two-dimensional detectors, where multiple rows (two or more rows) of detectors sit next to one another, have been introduced. In CT there have been significant problems for image reconstruction especially for two-dimensional detectors. Data provided by the two-dimensional detectors will be referred to as cone-beam (CB) data or CB projections.

In addition to spiral scans there are non-spiral scans, in which the trajectory of the x-ray source is different from spiral. In medical imaging, non-spiral scans are frequently performed using a C-arm device, which is usually smaller and more portable than spiral type scanning systems. For example, C-arm scanning devices have been useful for being moved in and out of operating rooms, and the like.

FIG. 1 shows a typical prior art arrangement of a patient on a table that moves through a C-arm device, that is capable of rotating around the patient, having an x-ray tube source and a detector array, where cone beam projection data sets are received by the x-ray detector, and an image reconstruction process takes place in a computer with a display for the reconstructed image.

There are known problems with using C-arm devices to reconstruct data. See in particular for example, pages 755–759 of Kudo, Hiroyuki et al., Fast and Stable Cone-Beam Filtered Backprojection Method for Non-planar Orbits, IOP Publishing LTD, 1998, pages 747–760. The Kudo paper describes image reconstruction using C-arm devices for various shift-variant filtered back projection (FBP) structures, which are less efficient than convolution-based FBP algorithms.

For three-dimensional (also known as volumetric) image reconstruction from the data provided by spiral and non-spiral scans with two-dimensional detectors, there are two known groups of algorithms: Exact algorithms and Approximate algorithms, that each have known problems. Under ideal circumstances, exact algorithms can provide a replication of an exact image. Thus, one should expect that exact algorithms would produce images of good quality even under non-ideal (that is, realistic) circumstances.

However, exact algorithms can be known to take many hours to provide an image reconstruction, and can take up great amounts of computer power when being used. These algorithms can require keeping considerable amounts of cone beam projections in memory.

Approximate algorithms possess a filtered back projection (FBP) structure, so they can produce an image very efficiently and using less computing power than Exact algorithms. However, even under the ideal circumstances these algorithms produce an approximate image that may be similar to but still different from the exact image. In particular, Approximate algorithms can create artifacts, which are false features in an image. Under certain circumstances and conditions these artifacts could be quite severe.

To date, there are no known algorithms that can combine the beneficial attributes of Exact and Approximate algorithms into a single algorithm that is capable of replicating an exact image under the ideal circumstances, uses small amounts of computer power, and reconstructs the exact images in an efficient manner (i.e., using the FBP structure) in the cases of complete circle and line and incomplete circle and line scanning.

If the C-arm rotates 360 degrees around the patient, this produces a complete circle. If the C-arm rotates less than 360 degrees around the patient, this produces an incomplete circle. In what follows, the word circle covers both complete and incomplete cases. Here and everywhere below by the phrase that the algorithm of the invention reconstructs an exact image we will mean that the algorithm is capable of reconstructing an exact image. Since in real life any data contains noise and other imperfections, no algorithm is capable of reconstructing an exact image.

Image reconstruction has been proposed in many U.S. Patents. See for example, U.S. Pat. Nos. 5,663,995 and 5,706,325 and 5,784,481 and 6,014,419 to Hu; U.S. Pat. Nos. 5,881,123 and 5,926,521 and 6,130,930 and 6,233,303 to Tam; U.S. Pat. No. 5,960,055 to Samaresekera et al.; U.S. Pat. No. 5,995,580 to Schaller; U.S. Pat. No. 6,009,142 to Sauer; U.S. Pat. No. 6,072,851 to Sivers; U.S. Pat. No. 6,173,032 to Besson; U.S. Pat. No. 6,198,789 to Dafni; U.S. Pat. No. 6,215,841 and U.S. Pat. No. 6,266,388 to Hsieh. Other U.S. patents have proposed for image reconstruction as well. See U.S. Pat. No. 6,504,892 to Ning; U.S. Pat. No. 6,148,056 to Lin; U.S. Pat. No. 5,784,481 to Hu; U.S. Pat. No. 5,706,325 to Hu; and U.S. Pat. No. 5,170,439 to Zeng et al.

However, none of the patents overcome all of the deficiencies to image reconstruction referenced above. The inventor is not aware of any known processes, methods and systems that combines the beneficial attributes of Exact and Approximate algorithms into a single algorithm that is capable of replicating an exact image under the ideal circumstances, uses small amounts of computer power, and reconstructs the exact images in an efficient manner (i.e., using the FBP structure) in the cases of complete circle and line and incomplete circle and line scanning.

SUMMARY OF THE INVENTION

A primary objective of the invention is to provide improved processes, methods and systems for reconstructing images of objects that have been scanned with two-dimensional detectors.

A secondary objective of the invention is to provide improved processes, methods and systems for reconstructing images of objects scanned with a circle and line x-ray source trajectory that is able to reconstruct an exact image and not an approximate image.

A third objective of the invention is to provide improved processes, methods and systems for reconstructing images of objects scanned with a circle and line x-ray source trajectory that creates an exact image in an efficient manner using a filtered back projection (FBP) structure.

A fourth objective of the invention is to provide improved processes, methods and systems for reconstructing images of objects scanned with a circle and line x-ray source trajectory that creates an exact image with minimal computer power.

A fifth objective of the invention is to provide improved processes, methods and systems for reconstructing images of objects scanned with a circle and line x-ray source trajectory that creates an exact image utilizing a convolution-based FBP structure.

A sixth objective of the invention is to provide improved processes, methods and systems for reconstructing images of objects scanned with a circle and line x-ray source trajectory that is CB projection driven allowing for the algorithm to work simultaneously with the CB data acquisition.

A seventh objective of the invention is to provide improved processes, methods and systems for reconstructing images of objects scanned with a circle and line x-ray source trajectory that does not require storing numerous CB projections in computer memory.

An eighth objective of the invention is to provide improved processes, methods and systems for reconstructing images of objects scanned with a circle and line x-ray source trajectory that allows for almost real time imaging to occur where images are displayed as soon as a slice measurement is completed.

A preferred embodiment of the invention uses a seven overall step process for reconstructing the image of an object under a circle and line scan. In a first step a current CB projection is measured. Next, a family of lines is identified on a detector according to a novel algorithm. Next, a computation of derivatives between neighboring projections occurs and is followed by a convolution of the derivatives with a filter along lines from the selected family of lines. Next, using the filtered data, the image is updated by performing back projection. Finally, the preceding steps are repeated for each CB projection until an entire object has been scanned. This embodiment works with keeping several (approximately 2–4) CB projections in memory at a time and uses one family of lines.

The invention is not limited to an object that undergoes a scan consisting of a single circle and a single line segment. The invention can be applied to trajectories consisting of several circles and line segments by applying it to various circle and line pairs, and then combining the results.

The circle and line scanning can include a partial planar curve scan before or after a line scan. The planar curved scan can be less than a full circle and even greater than a full circle. Additional and subsequent circle and line scans can be done consecutively after a first circle and line scan.

Further objects and advantages of this invention will be apparent from the following detailed description of the presently preferred embodiments, which are illustrated schematically in the accompanying drawings.

BRIEF DESCRIPTION OF THE FIGURES

FIG. 9 is a three substep flow chart for identifying the set of lines, which corresponds to step 20 of FIG. 2.

FIG. 10 is a seven substep flow chart for preparation for filtering, which corresponds to step 40 of FIG. 2.

FIG. 11 is a seven substep flow chart for filtering, which corresponds to step 50 of FIG. 2.

FIG. 12 is an eight substep flow chart for backprojection, which corresponds to step 60 of FIG. 2.

DESCRIPTION OF THE PREFERRED EMBODIMENTS

Before explaining the disclosed embodiments of the present invention in detail it is to be understood that the invention is not limited in its application to the details of the particular arrangements shown since the invention is capable of other embodiments. Also, the terminology used herein is for the purpose of description and not of limitation.

Figure 1:
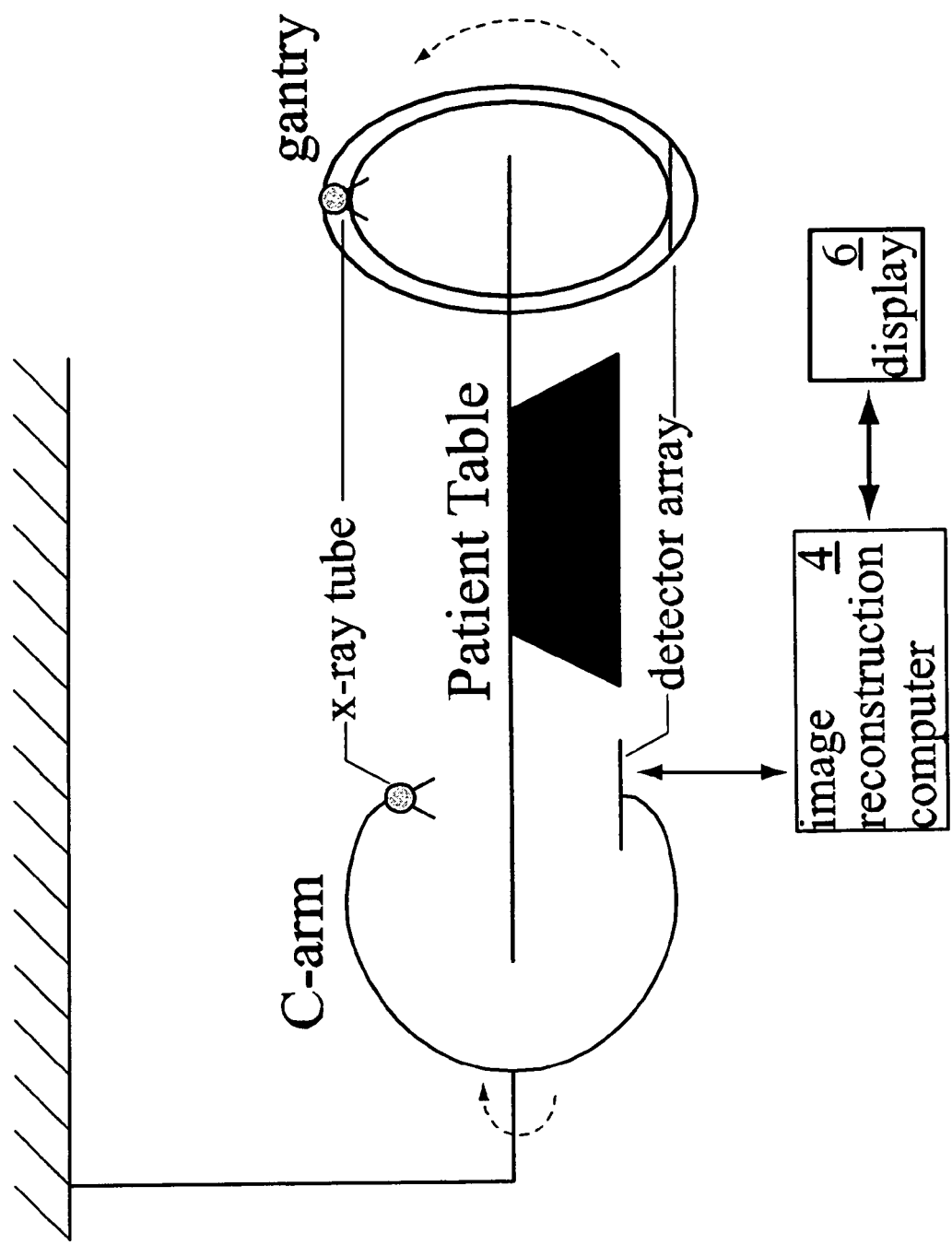
FIG. 1 shows a typical prior art view arrangement of a patient on a table that moves through a C-arm device, that is capable of rotating around the patient, having an x-ray tube source and a detector array, where cone beam projection data sets are received by the x-ray detector, and an image reconstruction process takes place in a computer with a display for the reconstructed image.

This invention is a Continuation-In-Part of U.S. patent application Ser. No. 10/728, 136, filed Dec. 4, 2003 which claims the benefit of priority to U.S. Provisional Application Ser. No. 60/430,802 filed, Dec. 4, 2002, and is a Continuation-In-Part of U.S. patent application Ser. No. 10/389,534 filed Mar. 14, 2003 which is a Continuation-In-Part of Ser. No. 10/389,090 filed Mar. 14, 2003, which is a Continuation-In-Part of Ser. No. 10/143,160 filed May 10, 2002 now U.S. Pat. No. 6,574,299, which claims the benefit of priority to U.S. Provisional Application 60/312,827 filed Aug. 16, 2001, all of which are incorporated by reference As previously described, FIG. 1 shows a typical prior art view arrangement of a patient on a table that moves through a C-arm device such as the AXIOM Artis MP, manufactured by Siemens, that is capable of rotating around the patient, having an x-ray tube source and a detector array, where CB projections are received by the x-ray detector, and an image reconstruction process takes place in a computer 4 with a display 6 for displaying the reconstructed image. For the subject invention, the detector array is a two-dimensional detector array. For example, the array can include two, three or more rows of plural detectors in each row. If three rows are used with each row having ten detectors, then one CB projection set would be thirty individual x-ray detections.

Alternatively, a conventional gantry, such as ones manufactured by Siemens, Toshiba, General Electric, and the like, can be used, as shown by the dotted concentric lines, for the X-ray sources and detector array. The gantry can rotate partially, and up to a full circle, or greater than a full circle.

Figure 2:
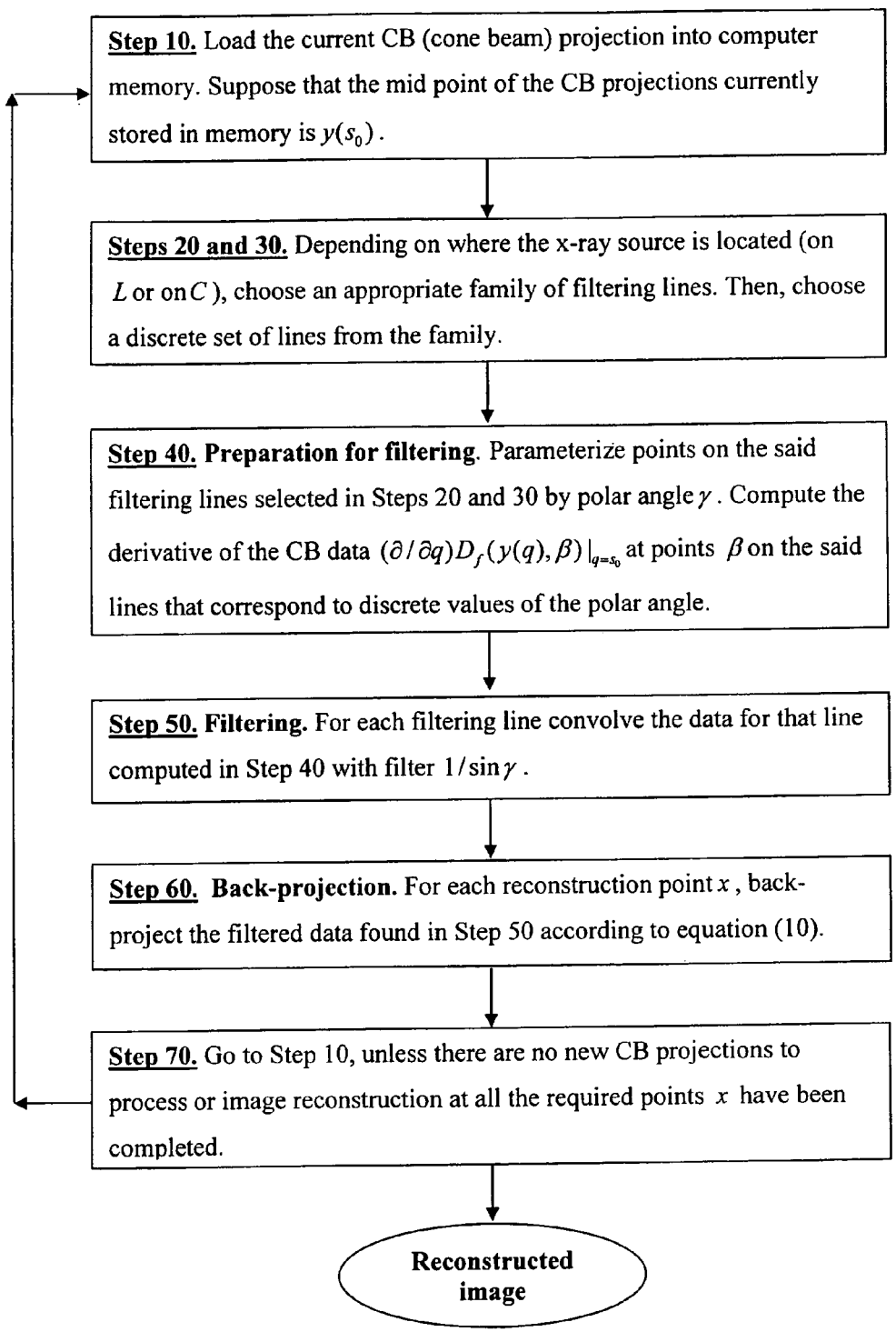
FIG. 2 shows an overview of the basic process steps of the invention.

FIG. 2 shows an overview of the basic process steps of the invention that occur during the image reconstruction process occurring in the computer 4 using a first embodiment. An overview of the invention process will now be described.

A preferred embodiment works with keeping several (approximately 2 to approximately 4) CB projections in computer memory at a time and uses one family of lines.

In the first step 10, a current CB(cone beam) projection set is taken. The next steps 20 and 30 identify sets of lines on a virtual x-ray detector array according to the novel algorithm, which will be explained later in greater detail. In the given description of the algorithm the detector array can be considered to be flat, so the selected line can be a straight tilted line across the array.

The next step 40 is the preparation for the filtering step, which includes computations of the necessary derivative of the CB projection data for the selected lines.

The next step 50 is the convolution of the computed derivative (the processed CB data) with a filter along lines from the selected family of lines. This step can also be described as shift-invariant filtering of the derivative of the CB projection data. In the next step 60, the image of the object being computed is updated by performing back projection. In the final step 70 it is indicated that the above steps 10–60 are repeated, unless image reconstruction is completed or there are no more CB projections to process.

The invention will now be described in more detail by first describing the main inversion formula followed by the novel algorithm of the invention.

Figure 3:
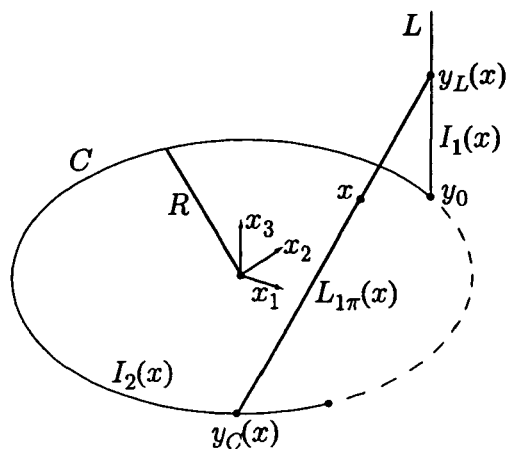
FIG. 3 shows mathematical notations of the circle and line scan.

Referring to FIG. 3, we consider a source trajectory consisting of a circle C and a line segment L attached to C. FIG. 3, shows mathematical notations of the scan. Let $y_0$ be the point where they intersect. Such a trajectory can be implemented with a C-arm by first moving the patient and then rotating the C-arm around the patient.

We suppose $I_1 \ni s \to y(s) \in L$ and $I_2 \ni s \to y(s) \in C$ are parameterizations of the line and circle, respectively. Here s is a real parameter, and y(s) is a point on the trajectory representing the x-ray source position. We assume that the circle is of radius R and centered at the origin. Let U be an open set, such that $$U \subset \{(x_1, x_2, x_3) \in U : x_1^2 + x_2^2 < R^2\}.$$

Next, we pick a reconstruction point $x \in U$, and consider the plane $\Pi(x)$ through x and L. $\Pi(x)$ intersects C at two points. One of them is $y_0$, and the second is denoted $y_C(x)$.

Let $L_{1\pi}(x)$ be the line segment containing x and connecting $y_C(x)$ to L. Then $y_L(x) \in L$ denotes the other endpoint of $L_{1\pi}(x)$. Our procedure determines two parametric intervals. The first one $I_1(x) \subset I_1$ corresponds to the section of L between $y_0$ and $y_L(x)$. The second one $I_2(x) \subset I_2$ corresponds to the section of C between $y_0$ and $y_C(x)$.

We use the following notations in equations 1 and 2 as follows:

$$D_f(y, \Theta) := \int_0^\infty f(y + \Theta t)\,dt,\ \Theta \in S^2; \qquad (1)$$

$$\beta(s, x) := \frac{x - y(s)}{|x - y(s)|},\ x \in U,\ s \in I_1 \cup I_2. \qquad (2)$$

where
$S^2$ is the unit sphere,
$f$ is the function representing the distribution of the x-ray attenuation coefficient inside the object being scanned,
$\Theta$ is a unit vector,
$D_f(y, \Theta)$ is the cone beam transform of $f$,
$\beta(s, x)$ is the unit vector from the focal point y(s) pointing towards the reconstruction point x.

Figure 4:
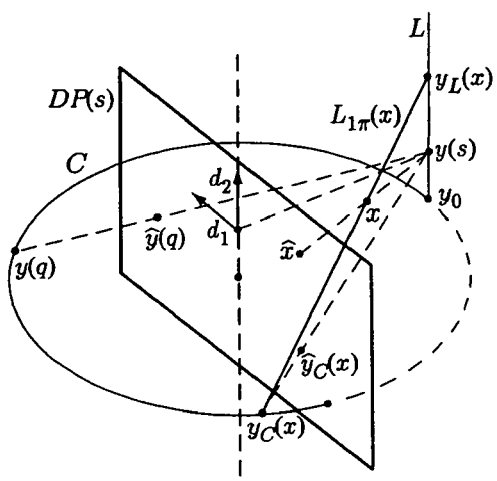
FIG. 4 illustrates a stereographic projection from the current source position on to the detector plane used in the algorithm for the invention.

Next, we suppose first $s \in I_1(x)$. Project x and C onto the detector plane DP(s) as shown in FIG. 4. Let h be the height of y(s) above the plane of the circle. We assume that DP(s) contains the z-axis and perpendicular to the shortest line segment connecting y(s) and DP(s). It is convenient to introduce the coordinate system on DP(s), in which the origin is at (0,0,h), the first axis is horizontal, and the second axis is vertical. In terms of the coordinates on DP(s) that we have just introduced the equation of $\hat{C}$ is given by equation 3.

$$d_2 = -\frac{h}{2}\left(\left(\frac{d_1}{R}\right)^2 + 1\right). \qquad (3)$$

Figure 5:
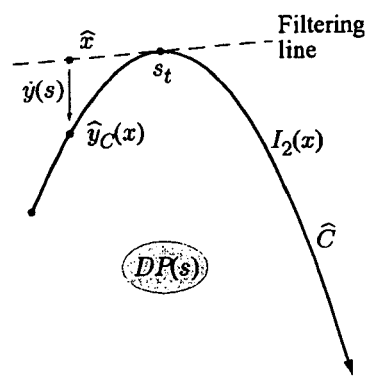
FIG. 5 illustrates finding of a filtering line for a reconstruction point x when the x-ray source is on the line.

Consequently, the projected circle $\hat{C}$ is a parabola, which opens downward. As is seen from FIG. 4, $\hat{x}$ is located above $\hat{C}$. By construction, $\hat{y}_C(x) \in \hat{C}$ and is located directly underneath $\hat{x}$ (see FIGS. 4 and 5). We find a plane through x and y(s), which is tangent to C at some $y_t(s,x) \in I_2(x)$. This determines the unit vector by equation 4.

$$u_1(s, x) := \frac{(y_t(s, x) - y(s)) \times \beta(s, x)}{|(y_t(s, x) - y(s)) \times \beta(s, x)|},\ x \in U,\ s \in I_1(x). \qquad (4)$$

We now pick a source position y(s) on the circle, $s \in I_2(x)$, and define another unit vector by equation 5.

$$u_2(s, x) := \frac{\dot{y}(s) \times \beta(s, x)}{|\dot{y}(s) \times \beta(s, x)|},\ x \in U,\ s \in I_2(x). \qquad (5)$$

Figure 6:
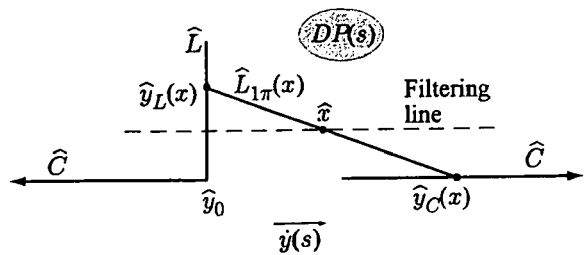
FIG. 6 illustrates finding of a filtering line for a reconstruction point x when the x-ray source is on the circle.

Here $\dot{y}(s)$ is the velocity vector of the source at the current position. The detector plane DP(s) corresponding to the source $y(s) \in C$ with various points and lines projected onto it is shown in FIG. 6. Using equations (6) and (7) we obtain the following reconstruction formula for $f \in C_0^\infty(U)$ by equation 6:

$$f(x) = -\frac{1}{2\pi^2} \sum_{k=1}^{2} \int_{I_k(x)} \frac{\delta_k(s,x)}{|x-y(s)|} \int_0^{2\pi} \frac{\partial}{\partial q} D_f(y(q), \Theta_k(s,x,\gamma)) \bigg|_{q=s} \frac{d\gamma}{\sin\gamma} ds, \quad (6)$$

where using equation 7

$$\Theta_k(s,x,\gamma) := \cos\gamma \beta(s,x) + \sin\gamma e_k(s,x), \; e_k(s,x) := \beta(s,x) \times u_k(s,x). \quad (7)$$

x is the cross-product of two vectors, q is parameter along the trajectory, and $\delta_k$ is defined by equation 8 as follows:

$$\delta_1(s, x) = -\text{sgn}(u_1(s,x)\cdot\dot{y}(s)), s\in I_1(x); \; \delta_2(s,x)=1, s\in I_2(x). \quad (8)$$

Suppose, for example, that L is parameterized in such a way that the source moves down along L as s increases. Then $\delta_1(s,x)=1, s\in I_1(x)$. If the source moves up along L as s increases, then $\delta_1(s,x)=-1, s\in I_1(x)$.

Figure 7:
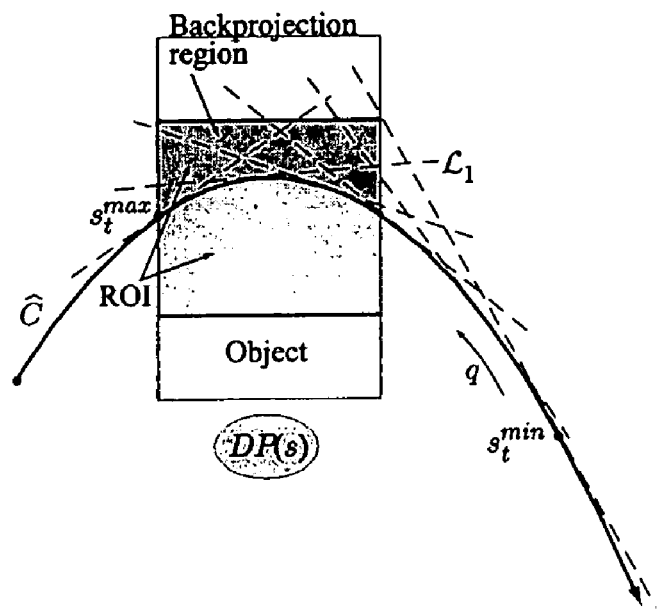
FIG. 7 illustrates a family of lines used in the algorithm of the invention corresponding to the case when the x-ray source is on the line.

We now describe an efficient (that is, of the convolution-based FBP type) implementation of inversion formula equation (6). Pick $y(s)\in L$. For a point $x\in U$ we have to find $s_1(s,x)\in I_2(x)$ (see FIG. 5). This determines the filtering line on the detector, which is tangent to $\hat{C}$ at $\hat{y}(s_t)$. Here and everywhere below by hat we indicate projection of a geometrical object (e.g., circle, line, point, etc.) onto a detector plane. Clearly, all other $x\in U$ which project onto this line to the left of $y(s_t)$ will share it as their filtering line. Hence, we can first perform filtering along lines on the detector tangent to $\hat{C}$ (see family $\_\_1$ in FIG. 7), and then perform backprojection. The range of $s_t$ values, $s_t^{min} \leq s_t \leq s_t^{max}$, depends on the region of interest (ROI) and is illustrated in FIG. 7. Suppose now $y(s)\in C$.

Under the invention filtering must be performed along lines on the detector parallel to $\hat{y}(s)$. The resulting family is denoted $\_\_2$ in FIG. 8. We pick any line from $\_\_2$. As is seen from FIG. 6, all x whose projection belongs to that line and appears to the right of $\hat{L}$ share it as their filtering line. As before, one can first perform filtering, Step 50, (which is shift-invariant) along these lines, and follow it by back projection, Step 60.

Let us describe this in more detail. It is clear that $s_t(s,x)$ actually depends only on s and $\beta(s,x)$. Therefore, we can write below including equations 9 and 10.

$$u_k(s,\beta) := u_k(s,x), \; e_k(s,\beta) := \beta \times u_k(s,\beta), \; k=1,2, \; \beta = \beta(s,x), \quad (9)$$

$$\Psi_k(s,\beta) := \int_0^{2\pi} \frac{\partial}{\partial q} D_f(y(q), \cos\gamma\beta + \sin\gamma e_k(s,\beta)) \bigg|_{q=s} \frac{1}{\sin\gamma} d\gamma,$$

$$f(x) = -\frac{1}{2\pi^2} \sum_{k=1}^{2} \int_{I_k(x)} \frac{\delta_k(s,x)}{|x-y(s)|} \Psi_k(s, \beta(s,x)) ds. \quad (10)$$

Any source position $y(s)$ and a filtering line from the corresponding family (either $\_\_1$ or $\_\_2$, depending on whether $y(s)\in L$ or $y(s)\in C$, determine a plane. We call it a filtering plane. Since $e(s,\beta)\cdot\beta=0, |e(s,\beta)|=1$, we can write equations 11 and 12.

$$\beta=(\cos\theta, \sin\theta); \; e_k(s,\beta)=(-\sin\theta, \cos\theta) \quad (11)$$

for all $\beta$, $e(s, \beta)$ confined to a filtering plane. Here $\theta$ denotes polar angle within a filtering plane. Therefore, $$\Psi_k(s,\beta) := \int_0^{2\pi} \frac{\partial}{\partial q} D_f(y(q), (\cos(\theta+\gamma), \sin(\theta+\gamma))) \bigg|_{q=s} \frac{1}{\sin\gamma} d\gamma \quad (12)$$

for all $\beta$ confined to a filtering plane.

Equation (12) is of convolution type and one application of Fast Fourier Transform (FFT) gives values of $\Psi_k(s, \beta)$ for all $\beta$ confined to a filtering plane at once. Equations (10) and (12) would represent that the resulting algorithm is of the convolution-based FBP type. This means that processing of every CB projection consists of two steps. First, shift-invariant and x-independent filtering along a family of lines on the detector is performed. Second, the result is back-projected to update the image matrix. A property of the back-projection step is that for any point $\hat{x}$ on the detector the value obtained by filtering at $\hat{x}$ is used for all points x on the line segment connecting the current source position $y(s)$ with $\hat{x}$. Since $\partial/\partial q$ in (12) is a local operation, each CB projection is stored in memory as soon as it has been acquired for a short period of time for computing this derivative at a few nearby points and is never used later.

Now we describe the algorithm in detail following the seven steps 10–70 shown in FIG. 2.

Step 10. We load the current CB(cone beam) projection into computer memory. Suppose that the mid point of the CB projections currently stored in memory is $y(s_0)$. The detector plane corresponding to the x-ray source located at $y(s_0)$ is denoted $DP(s_0)$.

Step 20. FIG. 9 is a three substep flow chart for identifying the set of lines, which corresponds to step 20 of FIG. 2. Here we assume that the x-ray source is located on the line L. Referring to FIG. 7, the set of lines can be selected by the following substeps 21, 22, and 23.

Step 21. Choose a discrete set of values of the parameter s, inside the interval $[s_t^{min}, s_t^{max}]$.

Step 22. For each $s_t$ chosen in Step 21 find a line tangent to the projected circle $\hat{C}$.

Step 23. The collection of lines constructed in Step 22 is the required set of lines (see FIG. 7 which illustrates the family of lines used in the algorithm of the invention).

Figure 8:
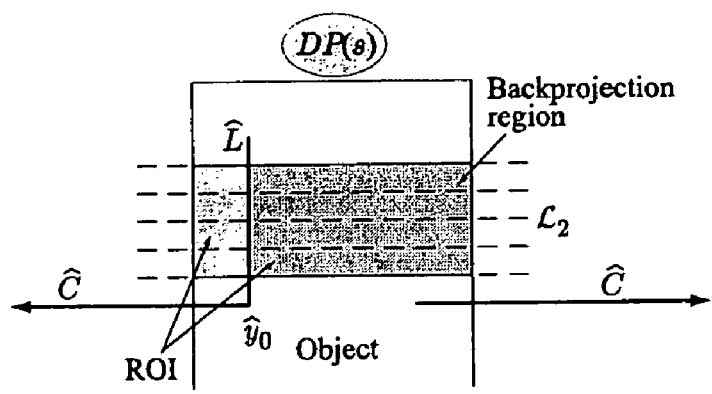
FIG. 8 illustrates a family of lines used in the algorithm of the invention corresponding to the case when the x-ray source is on the circle.

Step 30. Here we assume that the x-ray source is located on the circle C. Referring to FIG. 8, we form a set of lines parallel to the projection of the circle that cover the projection of the region of interest (ROI) inside the object being scanned.

Step 40. Preparation for filtering

FIG. 10 is a seven substep flow chart for preparation for filtering, which corresponds to step 40 of FIG. 2, which will now be described.

Step 41. If the x-ray source is located on the line L, fix a filtering line $L_{flt}\in\_\_1$ from the set of lines obtained in Step 20. If the x-ray source is located on the circle C, fix a filtering line $L_{flt}\in\_\_2$ from the set of lines obtained in Step 30.

Step 42. Parameterize points on the said line by polar angle $\gamma$ in the plane through $y(s_0)$ and $L_{flt}$.

Step 43. Choose a discrete set of equidistant values $\gamma_j$ that will be used later for discrete filtering in Step 50.

Step 44. For each $\gamma_j$ find the unit vector $\beta_j$ which points from $y(s_0)$ towards the point on $L_{flt}$ that corresponds to $\gamma_j$.

Step 45. Using the CB projection data $D_f(y(q),\Theta)$ for a few values of q close to $s_0$ find numerically the derivative $(\partial/\partial q)D_f(y(q),\Theta)|_{q=s_0}$ for all $\Theta=\beta_j$.

Step 46. Store the computed values of the derivative in computer memory.

Step 47. Repeat Steps 41–46 for all lines $L_{flt}$. This way we will create the processed CB data $\Psi(s_0, \beta_j)$ corresponding to the x-ray source located at $y(s_0)$.

Step 50. Filtering

FIG. 11 is a seven substep flow chart for filtering, which corresponds to step 50 of FIG. 2, which will now be described.

Step 51. Fix a filtering line $L_{flt}$. If the x-ray source is located on the line L, we take $L_{flt}\epsilon_{-1}$. If the x-ray source is located on the circle C, we take $L_{flt}\epsilon_{-2}$.

Step 52. Compute FFT (Fast Fourier Transform) of the values of the said processed CB data computed in Step 40 along the said line.

Step 53. Compute FFT of the filter $1/\sin \gamma$

Step 54. Multiply FFT of the filter $1/\sin \gamma$ (the result of Steps 53) and FFT of the values of the said processed CB data (the result of Steps 52).

Step 55. Take the inverse FFT of the result of Step 54.

Step 56. Store the result of Step 55 in computer memory.

Step 57. Repeat Steps 51–56 for all lines in the said family of lines. This will give the filtered CB data $\Phi(s_0, \beta_j)$.

By itself the filtering step can be well known in the field and can be implemented, for example, as shown and described in U.S. Pat. No. 5,881,123 to Tam, which is incorporated by reference.

Step 60. Back-Projection

FIG. 12 is an eight substep flow chart for backprojection, which corresponds to step 60 of FIG. 2, which will now be described.

Step 61. Fix a reconstruction point x, which represents a point inside the patient where it is required to reconstruct the image.

Step 62. If $s_0$ belongs to $I_1(x) \cup I_2(x)$, then the said filtered CB data affects the image at x and one performs Steps 63–68. If $s_0$ is not inside $I_1(x) \cup I_2(x)$, then the said filtered CB data is not used for image reconstruction at x. In this case go back to Step 61 and choose another reconstruction point.

Step 63. Find the projection $\hat{x}$ of x onto the detector plane $DP(s_0)$ and the unit vector $\beta(s_0, x)$, which points from $y(s_0)$ towards x.

Step 64. Identify filtering lines $L_{flt}\epsilon_{-1}$ or $L_{flt}\epsilon_{-2}$ (depending on where the x-ray source is located) and points on the said lines that are close to the said projection $\hat{x}$. This will give a few values of $\Phi(s_0, \beta_j)$ for $\beta_j$ close to $\beta(s_0, x)$.

Step 65. With interpolation estimate the value of $\Phi(s_0, \beta(s_0, x))$ from the said values of $\Phi(s_0, \beta_j)$ for $\beta_j$ close to $\beta(s_0, x)$.

Step 66. Compute the contribution from the said filtered CB data to the image being reconstructed at the point x by multiplying $\Phi(s_0, \beta(s_0, x))$ by $-\delta_k(s_0, x)/(2\pi^2|x-y(s_0)|)$. The quantity $\delta_k(s_0, x)$ is defined by equation (8).

Step 67. Add the said contribution to the image being reconstructed at the point x according to a pre-selected scheme (for example, the Trapezoidal scheme) for approximate evaluation of the integral in equation (10).

Step 68. Go to Step 61 and choose a different reconstruction point x.

Step 70. Go to Step 10 (FIG. 2) and load the next CB projection into computer memory. The image can be displayed at all reconstruction points x for which the image reconstruction process has been completed (that is, all the subsequent CB projections are not needed for reconstructing the image at those points). Discard from the computer memory all the CB projections that are not needed for image reconstruction at points where the image reconstruction process has not completed. The algorithm concludes when the scan is finished or the image reconstruction process has completed at all the required points.

The invention is not limited to an object that undergoes a scan consisting of a single circle and a single line segment. The algorithm can be applied to trajectories consisting of several circles and line segments by applying it to various circle and line pairs, and then combining the results. The algorithm can be applied to trajectories in which a planar curve is not necessarily a circle, but, for example, an ellipse, and the like.

Other Embodiments of the invention are possible. For example, one can integrate by parts in equation (6) as described in the inventor's previous U.S. patent application Ser. No. 10/143,160 filed May 10, 2002 now U.S. Pat. No. 6,574,299, now incorporated by reference, to get an exact convolution-based FBP-type inversion formula which requires keeping only one CB projection in computer memory. The algorithmic implementation of this alternative embodiment can be similar to and include the algorithmic implementation of Embodiment Two in the inventor's previous U.S. patent application Ser. No. 10/143,160 filed May 10, 2002 now U.S. Pat. No. 6,574,299, now incorporated by reference. The corresponding equations will now be described.

Introduce the following notations in equation 13:

While the invention has been described with rotating C-arm type devices, the invention can be used with rotating gantry devices.

Furthermore, the amount of rotating can include a single rotational curve of at least approximately 5 degrees up to approximately 360 degrees or greater. Theoretically, there is no limit on the minimum range of rotation. Under realistic practical circumstances, a minimum range of rotation is between approximately 10 and approximately 20 degrees.

The circle and line scanning of an object can have a line scanning before or after a single rotational curve scan as defined above.

Subsequent circle and line scanning can occur as needed for image reconstruction.

Although the preferred embodiments describe applications of using x-ray sources for creating data for image reconstruction, the invention can be applicable with other sources that create line integral data for image reconstruction, such as but not limited to early arriving photons.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim:

1. A method of reconstructing images from data provided by at least one detector, comprising the steps of:

rotating a scanner in at least one curve within a plane about a stationary object while scanning the object;

scanning the object along a line transversal to the plane of said at least one curve;

storing at least 1 cone beam (CB) projection in memory at a time;

using at least one family of lines for the step of reconstructing;

applying a convolution based shift invariant Filtered Back Projection (FBP) algorithm to both the at least one curve within the plane and the line transversal to the plane of the at least one curve;

back projection updating the image of the scanned object to reconstruct an exact image of the scanned object with the convolution based FBP algorithm; and displaying the reconstructed image.

2. The method of claim 1, wherein the at least one curve includes the step of:

rotating a C-arm device about a portion of the object.

3. The method of claim 1, wherein the at least one curve includes the step of:

rotating a gantry about a portion of the object.

4. The method of claim 1, wherein the at least one curve includes the step of:

rotating between approximately 5 degrees up to approximately 360 degrees.

5. The method of claim 4, further comprising the step of:

rotating over approximately 360 degrees about the object.

6. The method of claim 1, wherein the rotating and the subsequently scanning the object include the steps of:

moving a table supporting the object through a C-arm device and rotating the C-arm around the object.

7. The method of claim 1, wherein the step of storing at least 1 cone beam (CB) projection includes the steps of:

storing approximately 2 to approximately 4 cone beam (CB) projections in memory at a time.

8. A method of reconstructing images from a planar curve scan and a line scan of an object, comprising the steps of:

(a) collecting cone beam (CB) data from a detector during the planar curve scan and the line scan of the object;

(b) identifying lines on a plane Π intersecting the cone beam, wherein the step (b) of identifying lines includes the steps of:

(bi) when an x-ray source belongs to the line scan, project the planar curve scan onto Π and choose a discrete set of lines tangent to that projection; and (bii) when the x-ray source belongs to the planar curve scan, project the planar curve scan onto Π and choose a discrete set of lines parallel to that projection;

(c) preprocessing and shift invariant filtering said data along said lines, wherein the step (c) of preprocessing includes computing the derivative $(\partial/\partial s)D_f(y(s),\Theta)$, wherein s is parameter along the scan path, which determines point y(s) on the said path, $D_f(y,\Theta)$ is the cone beam transform of $f$ corresponding to the x-ray source located at the point y and the direction Θ, $f$ is a function describing the object being scanned;

(d) back projecting said filtered data to form a precursor of said image;

(e) repeating steps a, b, c, and d until an image of the object is reconstructed; and (f) displaying the reconstructed image.

9. The method of claim 8, wherein shift-invariant filtering in step (c) includes convolving the derivative $(\partial/\partial s)D_f(y(s),\Theta)$ with kernel $1/\sin(\gamma)$ within a filtering plane containing y(s) and a line, identified in step (b) above, where γ is polar angle in the plane.

10. The method of claim 8, wherein the planar curve scan includes:

a complete circle about the object.

11. The method of claim 8, wherein the planar curve scan includes:

less than complete circle about the object.

12. The method of claim 8, wherein the back-projection step (d) includes the steps of:

(di) fix a reconstruction point x, which represents a point inside the object being scanned, to reconstruct the image;

(dii) when s belongs to I(x), then the said filtered CB data affects the image at x and one performs Steps (diii) to (dvii), and when s is not inside the interval I(x), then the said filtered CB data is not used for the image reconstruction at x and go back to step (di) and choose another reconstruction point, wherein I(x) is the parametric interval corresponding to the section of the scan path bounded by the PI-line of x; and PI-line of x is the line segment containing x, one endpoint of which belongs to the planar curve scan, and the other endpoint of which belongs to the line scan;

(diii) find the projection $\hat{x}$ of x onto a detector plane DP(s) and unit vector β(s,x), which points from y(s) towards x;

(div) estimate a value of Φ(s, β(s,x)), where Φ(s, β(s,x)) is the filtered CB data corresponding to the source position located at the point y(s) and direction β(s,x);

(dv) determine contribution from filtered CB data to the image being reconstructed at the point x by multiplying Φ(s, β(s,x)) by a weighting factor;

(dvi) add the said contribution to the image being reconstructed at the point x according to a pre-selected scheme; and (dvii) go to step (di) and choose a different reconstruction point x.

13. The method of claim 8, further comprising the steps of:

storing approximately 2 to approximately 4 cone beam (CD) projections in memory at a time; and using one family of lines for each x-ray source position for the step of filtering.

14. A method of computing images derived from a planar curve scan and a line scan, comprising the steps of:

(a) collecting cone beam (CB) data from a detector during a planar curve scan and line scan of an object;

(b) identifying lines on a plane Π intersecting the cone beam, wherein the step (b) of identifying lines includes the steps of:

(bi) when an the x-ray source belongs to the line portion of the scan, project the planar curve portion of the scan onto Π and choose a set of lines tangent to that projection; and (bii) when the x-ray source belongs to the planar curve portion of the scan, project the planar curve portion of the scan onto Π and choose a set of lines parallel to that projection;

(c) preprocessing and shift invariant filtering said data along said lines, wherein the step (c) of preprocessing includes computing the derivative of $D_f(y(s),\Theta)$ with respect to Θ along a direction non-parallel to the plane determined by y(s) and a filtering line, the said plane being a filtering plane, wherein s is parameter along the scan path, which determines point y(s) on the said path, $D_f(y,\Theta)$ is the cone beam transform of $f$ corresponding to the x-ray source located at the point y and the direction Θ, $f$ is a function describing the object being scanned;

(d) back projecting said filtered data to form a precursor of said image;
(e) repeating steps a, b, c, and d until an image of the object is reconstructed; and
(f) displaying the reconstructed image.

15. The method of claim 14, wherein shift-invariant filtering in step (c) includes convolving the data $D_f(y(s),\Theta)$ with kernel $1/\sin(\gamma)$ within a filtering plane, where $\gamma$ is polar angle in the plane.

16. The method of claim 14, wherein shift-invariant filtering in step (c) includes convolving the data $D_f(y(s),\Theta)$ with kernel $$\frac{\partial}{\partial \gamma} \frac{1}{\sin(\gamma)}$$

within a filtering plane, where $\gamma$ is polar angle in the plane.

17. The method of claim 14, wherein shift-invariant filtering in step (c) includes convolving the derivative of $D_f(y(s),\Theta)$ with a kernel within a filtering plane, the derivative of $D_f(y(s),\Theta)$ is the derivative with respect to $\Theta$ along a direction non-parallel to the filtering plane.

18. The method of claim 17, wherein y(s) belongs to the line portion of the scan.

19. The method of claim 17, wherein y(s) belongs to the planar curve portion of the scan.

20. The method of claim 14, wherein the planar curve scan includes:
a complete circle about the object.

21. The method of claim 14, wherein the planar curve scan includes;
less than complete circle about the object.

22. The method of claim 14, wherein the back-projection step (d) includes the steps of:
(di) fix a reconstruction point x, which represents a point inside the object being scanned, to reconstruct the image;
(dii) when s belongs to I(x), then the said filtered CB data affects the image at x and one performs Steps (diii) to (dvii) and when s is not inside the interval I(x), then the said filtered CB data is not used for the image reconstruction at x and go back to step (di) and choose another reconstruction point, wherein
I(x) is the parametric interval corresponding to the section of the scan path bounded by the PI-line of x; and
PI-line of x is the line segment containing x, one endpoint of which belongs to the planar curve scan, and the other endpoint of which belongs to the line scan;
(diii) find the projection $\hat{x}$ of x onto a detector plane DP(s) and unit vector $\beta(s,x)$, which points from y(s) towards x;
(div) estimate a value of $\Phi(s, \beta(s,x))$, where $\Phi(s, \beta(s,x))$ is the filtered CB data corresponding to the source position located at die point y(s) and direction $\beta(s,x)$;
(dv) determine contribution from filtered CB data to the image being reconstructed at the point x by multiplying $\Phi(s, \beta(s,x))$ by a weighting factor,
(dvi) add the said contribution to the image being reconstructed at the point x according to a pre-selected scheme; and
(dvii) go to step (di) and choose a different reconstruction point x.

23. The method of claim 14, further comprising the steps of:
storing 1 cone beam(CB) projection in memory at a time; and
using one family of lines for each x-ray source position for the step of filtering.

24. A method of reconstructing images from data provided by at least one detector, comprising the steps of:
scanning the object with a planar curved scan and a line scan by at least one detector;
storing at least one cone beam (CB) projection in memory at a time;
applying a convolution based shift invariant Filtered Back Projection (FBP) algorithm to both the planar curved scan and the line scan ;
back projection updating the image of the scanned object to reconstruct an exact image of the scanned object with the convolution based shift invariant FBP algorithm using at least one family of lines; and displaying the reconstructed image.

25. The method of claim 24, wherein the scanning step includes the step of:
scanning by the planar curved scan before the line scan.

26. The method of claim 24, wherein the scanning step includes the step of:
scanning by the line scan before the planar curved scan.

27. The method of claim 24, further comprising the step of:
providing a C-arm device for the scanning of the object.

28. The method of claim 24, further comprising the step of:
providing a gantry for the scanning of the object.

29. The method of claim 24, wherein the planar curve scan includes:
at least a full circle scan about the object.

30. The method of claim 24, wherein the planar curve scan includes:
less than a full circle scan about the object.

31. The method of claim 24, further comprising the step of:
consecutively scanning the object with another planar curve scan and another line scan.

32. A method of computing images of a scanned object derived from a planar curve scan and a line scan, comprising the steps of:
using at least one family of lines for the step of reconstructing;
applying a convolution based shift invariant Filtered Back Projection (FBP) algorithm to both the planar curved scan and the line scan;
backprojection updating the image of the scanned object to reconstruct an exact image of the scanned object with the convolution based shift invariant FBP algorithm, wherein the step of backprojection includes:
(a) fixing a reconstruction point x;
(b) identifying a line segment containing the point x, whose one endpoint $y_C(x)$ is on the curve scan, and the other endpoint $y_L(x)$ is on the line scan;
(c) for image reconstruction at x using those portions of the line scan cone beam data, which are on each side of $y_L(x)$; and
(d) repeating steps a, b, and c for all points x, displaying the reconstructed image.

* * * * *

UNITED STATES PATENT AND TRADEMARK OFFICE
CERTIFICATE OF CORRECTION

| | | |
|---|---|---|
| PATENT NO. | : 7,197,105 B2 | Page 1 of 1 |
| APPLICATION NO. | : 10/523867 | |
| DATED | : March 27, 2007 | |
| INVENTOR(S) | : Alexander Katsevich | |

It is certified that error appears in the above-identified patent and that said Letters Patent is hereby corrected as shown below:

Col. 1 lines 17-18 should read,

STATEMENT REGARDING FEDERALLY SPONSORED RESEARCH OR DEVELOPMENT

This subject invention was made with government support under the National Science Foundation, federal contract number DMS0104033. The government has certain rights in this invention.

Signed and Sealed this
Fifteenth Day of March, 2011

David J. Kappos
*Director of the United States Patent and Trademark Office*